United States Patent
Peters et al.

(10) Patent No.: US 6,514,712 B1
(45) Date of Patent: Feb. 4, 2003

(54) PROBE FOR THE EARLY DETECTION OF DISPLASIAS IN MULTILAYER TESSELATED EPITHELIUM AND FOR THE DIAGNOSIS AND THERAPY OF CARCINOMAS

(75) Inventors: Heiko Peters, Oberschleissheim (DE); Rudolf Balling, München (DE); Heinz Höfler, München (DE); Thomas Richter, Friedrichstrasse (DE)

(73) Assignee: GSF-Forschungszentrum fur Umwelt und Gesundheit GmbH, Oberschleissheim (DE)

( * ) Notice: Subject to any disclaimer, the term of this patent is extended or adjusted under 35 U.S.C. 154(b) by 0 days.

(21) Appl. No.: 08/930,830

(22) PCT Filed: Feb. 7, 1997

(86) PCT No.: PCT/EP97/00564
§ 371 (c)(1),
(2), (4) Date: Jan. 16, 1998

(87) PCT Pub. No.: WO97/30153
PCT Pub. Date: Aug. 21, 1997

(30) Foreign Application Priority Data

Feb. 12, 1996 (DE) .......................... 196 05 105

(51) Int. Cl.[7] ...................... G01N 33/53; G01N 33/574; C07K 16/00; C12P 21/08
(52) U.S. Cl. ........................ 435/7.23; 435/7.1; 435/810; 530/388.1; 530/388.8; 530/387.1
(58) Field of Search ........................... 530/387.1, 388.1, 530/388.8; 424/133.1; 435/7.1, 7.23, 810

(56) References Cited

U.S. PATENT DOCUMENTS 4,474,893 A * 10/1984 Reading
4,722,899 A * 2/1988 Hamaoka et al.

FOREIGN PATENT DOCUMENTS

DE 4225569 2/1994

OTHER PUBLICATIONS

Neubuesser et al. Sequence LIsting, Swiss Protein Database, US–08–930–2.rsp, 1995.*
Gura (Science, v278, 1997, pp. 1041–1042).*
Hol et al J Med Genetics vol. 33(8) 655–660, Aug. 1996.*
Balling et al Annals New York Acad Sci vol. 785 27–33, Jun. 1996.*
Ogasawara et al Development vol. 126 2539–2550, 1999.*
Muller et al Dev Biology vol. 178(2) 403–17, Sep. 1996.*
Seaver genetic Engineering News vol. 14(14) pp. 10 and 21, 1994.*
Seiver et al CLin Chemc vol. 27(11) 1797–1806, 1981.*
Marglin et al Ann Rev Biochem vol. 39 841–866, 1970.*
Lerner Nature vol. 299 592–596, 1982.*
Galfre et al Methods in Enzymology vol. 73 1–46, 1981.*
Dressler et al PNAS vol. 89 1179–1183, Feb. 1992.*
Nature Genetics, vol. 3, Nr. 4, Apr. 1993, pp. 292–298, Stapelton P. et al., "Chromosomal localization of seven PAX genes and cloning of a novel family member,".
EMBO Journal, vol. 12, Nr. 6, 1993, pp. 2361–2367, Maulbecker and Gruss, "The oncogenic potential of Pax genes."
Mammalian Genome, vol. 4, 1993, pp. 354–358, Wallin J. et al., "A new Pax gene, Pax–9 maps to mouse chromosome 12."
Development Biology, vol. 170, 1995, p. 701, 1995, Neubuser A. et al., "Characterization and developmental expression of Pax9, a paired–box containing gene related to Pax1."
Developmental Dynamics, vol. 203, Nr. 1, 1995, pp. 1–16, Peters H. et al., "Differential expression of the chick Pax–1 and Pax–9 gene: In situ hybridization and immunohistochemical analysis."
Mammalian Genome, vol. 8, 1997, pp. 62–64, Peters, "Isolation of the PAX9 cDNA from adult human esophagus."

* cited by examiner

Primary Examiner—Anthony C. Caputa
Assistant Examiner—Gary B. Nickol
(74) Attorney, Agent, or Firm—Nixon & Vanderhye P.C.

(57) ABSTRACT

The present invention provides a monoclonal or polyclonal antibody which specifically binds the Pax9 antigen as well as methods for using the same.

11 Claims, 8 Drawing Sheets

| | | | 90 |
|---|---|---|---|
HUPAX9  PAFGEVNQLG GVFVNGRPLP NAIRLRIVEL AQLGIRPCDI SRQLRVSHGC VSKILARYNE TGSILPGAIG GSKPRVITPT VVKHIRTYKQ

HUPAX9  RDPGIFAWEI RDRLLADGVC DKYNVPSVSS ISRILRNKIG NLAQQGHYDS YKQHQPTPQP ALPYNHIYSY PSPITAAAAK VPTPPGVPAI    180

HUPAX9  PGSVAMPRTW PSSHSVTDIL GIRSITDQVS DSSPYHSPKV EEWSSLGRNN FPAAAPHAVN GLEKGALEQE AKYGQAPNGL PAVGSFVSAS    270

HUPAX9  SMAPYTPAQ VSPYMTYSAA PSGYVAGHGW QHAGGTSLSP HNCDIPASLA FKGMQAAREG SHSVTAS    337

FIG.1A

```
HUPAX9  **PAFGEVNQ LGGVFVNGRP LPNAIRLRIV ELAQLGIRPC DISRQLRVSH GCVSKILARY NETGSILPGA IGGSKPRVTT PTVVKHIRTY   88
MPAX9   ME------- ---------- ---------- ---------- ---------- ---------- ---------- ---------- ----------   90

HUPAX9  KQRDPGIFAW EIRDRLLADG VCDKYNVPSV SSISRILRNK IGNLAQQGHY DSYKQHQPTP QPALPYNHIY SYPSPITAAA AKVPTPPGVP   178
MPAX9   ---------- ---------- ---------- ---------- ---------- -------A-- ---------- ---------- ----------   180

HUPAX9  AIPGSVAMPR TWPSSHSVTD ILGIRSITDQ /VSDSSPYHS PKVEEWSSLG RNNFPAAAPH AVNGLEKGAL EQEAKYGQAP NGLPAVGSFV   267
MPAX9   ---------L ---------- ---------- ----G----- ---------- ---------- ---------- ---------- -------S--   270

HUPAX9  SASSMAPYPT PAQVSPYMTY SAAPSGYVAG HGWQHAGGTS LSPHNCDIPA SLAFKGMQAA REGSHSVTAS **                      337
MPAX9   ---------- ---------- ---------- ----S-P--- ---------- ---------- ---------- AL●                    342
```

↑↓ : cloned in pMAL™-c2
— : identical amino acid
/ : missing amino acid
* : not sequenced
● : stop codon

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1013 base pairs
      (B) TYPE: nucleic acid (C) STRANDEDNESS: double
            (D) TOPOLOGY: circular (ii) MOLECULE TYPE: cDNA to mRNA (iii) HYPOTHETICAL: NO (iv) ANTI-SENSE: NO (v) FRAGMENT TYPE: C-terminal (vi) ORIGINAL SOURCE:
            (A) ORGANISM: Homo sapiens (ix) FEATURE:
            (A) NAME/KEY: CDS
            (B) LOCATION:3..1013

(xi) SEQUENCE DESCRIPTION: SEQ ID NO:1:

```
AG CCA GCC TTC GGG GAG GTG AAC CAG CTG GGA GGA GTG TTC GTG AAC        47
   Pro Ala Phe Gly Glu Val Asn Gln Leu Gly Gly Val Phe Val Asn
    1               5                  10                  15

GGG AGG CCG CTG CCC AAC GCC ATC CGG CTT CGC ATC GTG GAA CTG GCC       95
Gly Arg Pro Leu Pro Asn Ala Ile Arg Leu Arg Ile Val Glu Leu Ala
                20                  25                  30

CAA CTG GGC ATC CGA CCG TGT GAC ATC AGC CGC CAG CTA CGG GTC TCG      143
Gln Leu Gly Ile Arg Pro Cys Asp Ile Ser Arg Gln Leu Arg Val Ser
            35                  40                  45

CAC GGC TGC GTC AGC AAG ATC CTG GCG CGA TAC AAC GAG ACG GGC TCG      191
His Gly Cys Val Ser Lys Ile Leu Ala Arg Tyr Asn Glu Thr Gly Ser
        50                  55                  60

ATC TTG CCA GGA GCC ATC GGG GGC AGC AAG CCC CGG GTC ACT ACC CCC      239
Ile Leu Pro Gly Ala Ile Gly Gly Ser Lys Pro Arg Val Thr Thr Pro
    65                  70                  75

ACC GTG GTG AAA CAC ATC CGG ACC TAC AAG CAG AGA GAC CCC GGC ATC      287
Thr Val Val Lys His Ile Arg Thr Tyr Lys Gln Arg Asp Pro Gly Ile
 80                  85                  90                  95

TTC GCC TGG GAG ATC CGG GAC CGC CTG CTG GCG GAC GGC GTG TGC GAC      335
Phe Ala Trp Glu Ile Arg Asp Arg Leu Leu Ala Asp Gly Val Cys Asp
                100                 105                 110

AAG TAC AAT GTG CCC TCC GTG AGC TCC ATC AGC CGC ATT CTG CGC AAC      383
Lys Tyr Asn Val Pro Ser Val Ser Ser Ile Ser Arg Ile Leu Arg Asn
            115                 120                 125

AAG ATC GGC AAC TTG GCC CAG CAG GGT CAT TAC GAC TCA TAC AAG CAG      431
Lys Ile Gly Asn Leu Ala Gln Gln Gly His Tyr Asp Ser Tyr Lys Gln
        130                 135                 140

CAC CAG CCG ACG CCG CAG CCA GCG CTG CCC TAC AAC CAC ATC TAC TCG      479
His Gln Pro Thr Pro Gln Pro Ala Leu Pro Tyr Asn His Ile Tyr Ser
    145                 150                 155

TAC CCC AGC CCT ATC ACG GCG GCG GCC GCC AAG GTG CCC ACG CCA CCC      527
Tyr Pro Ser Pro Ile Thr Ala Ala Ala Ala Lys Val Pro Thr Pro Pro
160                 165                 170                 175

GGG GTG CCT GCC ATC CCC GGT TCG GTG GCC ATG CCG CGC ACC TGG CCC      575
Gly Val Pro Ala Ile Pro Gly Ser Val Ala Met Pro Arg Thr Trp Pro
                180                 185                 190

TCC TCG CAC TCC GTC ACC GAC ATC CTG GGC ATC CGC TCC ATC ACC GAC      623
Ser Ser His Ser Val Thr Asp Ile Leu Gly Ile Arg Ser Ile Thr Asp
            195                 200                 205

CAA GTG AGC GAC AGC TCC CCC TAC CAC AGC CCC AAG GTG GAG GAG TGG      671
Gln Val Ser Asp Ser Ser Pro Tyr His Ser Pro Lys Val Glu Glu Trp
        210                 215                 220

AGC AGC CTG GGC CGC AAC AAC TTC CCC GCC GCC GCC CCG CAT GCG GTG      719
Ser Ser Leu Gly Arg Asn Asn Phe Pro Ala Ala Ala Pro His Ala Val
    225                 230                 235
```

```
AAC GGG TTG GAG AAG GGA GCC CTG GAG CAG GAA GCC AAG TAC GGT CAG      767
Asn Gly Leu Glu Lys Gly Ala Leu Glu Gln Glu Ala Lys Tyr Gly Gln
240                 245                 250                 255

GCA CCA AAT GGT CTC CCA GCT GTG GGC AGT TTT GTG TCA GCA TCC AGC      815
Ala Pro Asn Gly Leu Pro Ala Val Gly Ser Phe Val Ser Ala Ser Ser
                260                 265                 270

ATG GCT CCT TAC CCT ACC CCA GCC CAA GTG TCG CCT TAC ATG ACC TAC      863
Met Ala Pro Tyr Pro Thr Pro Ala Gln Val Ser Pro Tyr Met Thr Tyr
                275                 280                 285

AGT GCT GCT CCT TCT GGT TAT GTT GCT GGA CAT GGG TGG CAA CAT GCT      911
Ser Ala Ala Pro Ser Gly Tyr Val Ala Gly His Gly Trp Gln His Ala
            290                 295                 300

GGG GGC ACC TCA TTG TCT CCC CAC AAC TGT GAC ATT CCG GCA TCG CTG      959
Gly Gly Thr Ser Leu Ser Pro His Asn Cys Asp Ile Pro Ala Ser Leu
305                 310                 315

GCG TTC AAG GGA ATG CAG GCA GCC AGA GAA GGT AGT CAT TCT GTC ACG     1007
Ala Phe Lys Gly Met Gln Ala Ala Arg Glu Gly Ser His Ser Val Thr
320                 325                 330                 335

GCT TCC                                                             1013
Ala Ser (2) INFORMATION FOR SEQ ID NO:2:

(i) SEQUENCE CHARACTERISTICS:
        (A) LENGTH: 337 amino acids
        (B) TYPE: amino acid
        (D) TOPOLOGY: linear (ii) MOLECULE TYPE: protein (xi) SEQUENCE DESCRIPTION: SEQ ID NO:2:

Pro Ala Phe Gly Glu Val Asn Gln Leu Gly Gly Val Phe Val Asn Gly
 1               5                  10                  15

Arg Pro Leu Pro Asn Ala Ile Arg Leu Arg Ile Val Glu Leu Ala Gln
                20                  25                  30

Leu Gly Ile Arg Pro Cys Asp Ile Ser Arg Gln Leu Arg Val Ser His
            35                  40                  45

Gly Cys Val Ser Lys Ile Leu Ala Arg Tyr Asn Glu Thr Gly Ser Ile
     50                  55                  60

Leu Pro Gly Ala Ile Gly Gly Ser Lys Pro Arg Val Thr Thr Pro Thr
65                  70                  75                  80

Val Val Lys His Ile Arg Thr Tyr Lys Gln Arg Asp Pro Gly Ile Phe
                85                  90                  95

Ala Trp Glu Ile Arg Asp Arg Leu Leu Ala Asp Gly Val Cys Asp Lys
                100                 105                 110

Tyr Asn Val Pro Ser Val Ser Ser Ile Ser Arg Ile Leu Arg Asn Lys
            115                 120                 125

Ile Gly Asn Leu Ala Gln Gln Gly His Tyr Asp Ser Tyr Lys Gln His
130                 135                 140

Gln Pro Thr Pro Gln Pro Ala Leu Pro Tyr Asn His Ile Tyr Ser Tyr
145                 150                 155                 160

Pro Ser Pro Ile Thr Ala Ala Ala Lys Val Pro Thr Pro Pro Gly
                165                 170                 175

Val Pro Ala Ile Pro Gly Ser Val Ala Met Pro Arg Thr Trp Pro Ser
            180                 185                 190

Ser His Ser Val Thr Asp Ile Leu Gly Ile Arg Ser Ile Thr Asp Gln
        195                 200                 205
```

```
Val Ser Asp Ser Ser Pro Tyr His Ser Pro Lys Val Glu Glu Trp Ser
    210                 215                 220
Ser Leu Gly Arg Asn Asn Phe Pro Ala Ala Ala Pro His Ala Val Asn
225                 230                 235                 240
Gly Leu Glu Lys Gly Ala Leu Glu Gln Glu Ala Lys Tyr Gly Gln Ala
                245                 250                 255
Pro Asn Gly Leu Pro Ala Val Gly Ser Phe Val Ser Ala Ser Ser Met
            260                 265                 270
Ala Pro Tyr Pro Thr Pro Ala Gln Val Ser Pro Tyr Met Thr Tyr Ser
        275                 280                 285
Ala Ala Pro Ser Gly Tyr Val Ala Gly His Gly Trp Gln His Ala Gly
290                 295                 300
Gly Thr Ser Leu Ser Pro His Asn Cys Asp Ile Pro Ala Ser Leu Ala
305                 310                 315                 320
Phe Lys Gly Met Gln Ala Ala Arg Glu Gly Ser His Ser Val Thr Ala
                325                 330                 335
Ser
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA-Oligonucleotide"

(xi) SEQUENCE DESCRIPTION: SEQ ID NO:3:

CCCAAGCTTT GGACGCTCCC ATCAGAGTGC                      30

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA-Oligonucleotide"

(xi) SEQUENCE DESCRIPTION: SEQ ID NO:4:

CCCAAGCTTA GCCAGCCTTC GGGGAGGTG                      29

(2) INFORMATION FOR SEQ ID NO:5:

(i) SEQUENCE CHARACTERISTICS:
        (A) LENGTH: 342 amino acids
        (B) TYPE: amino acid
        (D) TOPOLOGY: linear (ii) MOLECULE TYPE: protein (xi) SEQUENCE DESCRIPTION: SEQ ID NO:5:

```
Met Glu Pro Ala Phe Gly Glu Val Asn Gln Leu Gly Gly Val Phe Val
1               5                   10                  15
Asn Gly Arg Pro Leu Pro Asn Ala Ile Arg Leu Arg Ile Val Glu Leu
                20                  25                  30
Ala Gln Leu Gly Ile Arg Pro Cys Asp Ile Ser Arg Gln Leu Arg Val
            35                  40                  45
```

-continued

```
Ser His Gly Cys Val Ser Lys Ile Leu Ala Arg Tyr Asn Glu Thr Gly
    50                  55                  60
Ser Ile Leu Pro Gly Ala Ile Gly Gly Ser Lys Pro Arg Val Thr Thr
65                  70                  75                  80
Pro Thr Val Val Lys His Ile Arg Thr Tyr Lys Gln Arg Asp Pro Gly
                85                  90                  95
Ile Phe Ala Trp Glu Ile Arg Asp Arg Leu Leu Ala Asp Gly Val Cys
                100                 105                 110
Asp Lys Tyr Asn Val Pro Ser Val Ser Ser Ile Ser Arg Ile Leu Arg
            115                 120                 125
Asn Lys Ile Gly Asn Leu Ala Gln Gln Gly His Tyr Asp Ser Tyr Lys
        130                 135                 140
Gln His Gln Pro Ala Pro Gln Pro Ala Leu Pro Tyr Asn His Ile Tyr
145                 150                 155                 160
Ser Tyr Pro Ser Pro Ile Thr Ala Ala Ala Lys Val Pro Thr Pro
                165                 170                 175
Pro Gly Val Pro Ala Ile Pro Gly Ser Val Ala Leu Pro Arg Thr Trp
                180                 185                 190
Pro Ser Ser His Ser Val Thr Asp Ile Leu Gly Ile Arg Ser Ile Thr
        195                 200                 205
Asp Gln Gly Val Ser Asp Ser Ser Pro Tyr His Ser Pro Lys Val Glu
    210                 215                 220
Glu Trp Ser Ser Leu Gly Arg Asn Asn Phe Pro Ala Ala Ala Pro His
225                 230                 235                 240
Ala Val Asn Gly Leu Glu Lys Gly Ala Leu Glu Gln Glu Ala Lys Tyr
                245                 250                 255
Gly Gln Ala Pro Asn Gly Leu Pro Ala Val Ser Ser Phe Val Ser Ala
                260                 265                 270
Ser Ser Met Ala Pro Tyr Pro Thr Pro Ala Gln Val Ser Pro Tyr Met
        275                 280                 285
Thr Tyr Ser Ala Ala Pro Ser Gly Tyr Val Ala Gly His Gly Trp Gln
    290                 295                 300
His Ala Gly Ser Thr Pro Leu Ser Pro His Asn Cys Asp Ile Pro Ala
305                 310                 315                 320
Ser Leu Ala Phe Lys Gly Met Gln Ala Ala Arg Glu Gly Ser His Ser
                325                 330                 335
Val Thr Ala Ser Ala Leu
                340
```

PROBE FOR THE EARLY DETECTION OF DISPLASIAS IN MULTILAYER TESSELATED EPITHELIUM AND FOR THE DIAGNOSIS AND THERAPY OF CARCINOMAS

The present application is a 371 of PCT/EP97/00564, filed Feb. 7, 1997.

The present invention relates to a novel therapeutic or diagnostic agent containing as an active ingredient at least one nucleic acid and which is particularly useful for the early diagnosis of dysplasias of the stratified squamous epithelium and the cartilage as well as for tumour diagnosis and tumour therapy.

Squamous Epithelial Carcinomas Precancerous Stages and Dysplasias

The squamous epithelial carcinoma is the type of oesophageal tumour having the highest incidence. In tumour diagnostics, this tumour type has been classified on the basis of histological criteria into four categories (G1, G2, G3, and G4) wherein the occurrence of histopathological abnormalities is least in G1 tumours and highest in G4 tumours.

Great efforts have been made in medical research to develop suitable methods for tumour therapy. This research has been based on a comprehensive morphological, histological, and molecular tumour diagnosis as well as on the investigation of the generation of tumours. The molecular etiology of tumour generation is not homogenous—however, in a high number of cases mutations (deletions, gene amplifications, translocations of chromosomal portions, etc.) can be detected in the respective tissues which gradually manifest themselves in abnormal differentiation and eventually in uncontrolled cell divisions. In the squamous epithelial carcinomas of the oesophagus, a variety of mutations of oncogenes, tumour suppressor genes, and growth factor genes has been reported (see review in Stemmermann et al., 1994). Interestingly, such mutations were also detected in the tissues adjacent to the tumour which appeared to be histologically normal. It has been assumed that for a tumour to develop the entirety of intracellular damages must exceed a critical threshold value. Therefore, a successful tumour therapy will also depend on its ability to diagnose early stages of tumour development.

From a histopathological point of view, dysplasias of the stratified squamous epithelium are precancerogenic lesions and, thus, may represent potential early stages of tumour development. One of the reasons for the development of dysplasias is the degeneration of the transcriptional control of differentiation-specific genes. Normally, this control is ensured by an orderly co-operation of transcription factors which jointly regulate the activity of these target genes. If it would be possible to show an alteration of already the expression, subcellular localization, or activity, respectively, of these transcription factors, then, these findings might be used as diagnostic markers for an early diagnosis of dysplasias. Regarding squamous epithelial tumours, a useful marker should also be able to indicate an alteration of the expression in malignant tissue.

Pax Genes

Pax genes are members of a multigene family containing a conserved DNA sequence called the "paired" box. To date, 9 different Pax genes (Pax1–Pax9) have been isolated from the genomes of humans and mouse (see review in Walther et al., 1991; Stapleton et al., 1993; Wallin et al., 1993). In addition, the "paired" box has also been detected in members of lower classes of animals such as nematodes, drosophila, zebrafish, turtles and chicken (see review in Noll, 1993). The "paired" box codes for the DNA-binding "paired" domain; thus, the proteins encoded by the Pax genes may be assigned to the class of transcription factors (Treisman et al., 1991; Chalepakis et al., 1991; Xu et al., 1995).

Pax genes play an important role in the development of embryonic structures. During the development of the mouse embryo, Pax genes are expressed spatially as well as temporally in specific patterns which partly overlap each other (Gruss & Walther, 1992). The strong instructive effect of the Pax genes during embryogenesis could be demonstrated i.a. by ectopic expression of Pax6 in the imaginal discs of drosophila wings and legs, respectively, using genetic engineering (normally, the Pax6 gene is expressed in the eye primordium). By ectopic Pax6 expression in the imaginal discs of wings or legs, respectively, a nearly complete eye develops in a wrong site (Halder et al., 1995).

By the finding that mutations in Pax genes cause congenital defects in mice but also in men (Pax1: undulated; Pax3: splotch and Waardenburg syndrome; Pax6: small eye and aniridia) the studies performed on this group of genes gained further interest (Balling et al., 1988; Epstein et al., 1991; Tassabehji et al., 1992; Hill et al., 1991; Ton et al., 1991).

The function of the Pax genes is not restricted to embryogenesis. For example, it could be shown that Pax5 protein activates the CD19 gene (CD19 codes for a protein specific for B lymphocytes) (Kozmik et al., 1992), and therefore has also functions in the adult organism. Pax8 is expressed in the thyroid of the adult organism and is involved in the activation of the thyroglobulin and thyroperoxidase genes (Zannini et al., 1992).

Pax Genes and Tumour Development

Some of the members of the family of Pax genes (Pax1, Pax2, Pax3, Pax6, Pax8) have been identified as proto-oncogenes due to their tumourigenic properties. This identification has been based on transformation tests in which the above-mentioned Pax genes are overexpressed in NIH3T3 cells or 208 cells, respectively, under the control of the cytomegalovirus promoter. Injection of the transformed 208 cells into nude mice caused sarcomas to occur in almost all of the cases (Maulbecker & Gruss, 1993).

The molecular basis for the development of tumours by activation of Pax genes is unknown. It could be shown for a number of rhabdomyosarcomas that as a result of chromosomal translocations Pax3 or Pax7 become fused to the FKHR gene, a transcription factor of the family of forkhead genes. It has been demonstrated that chimeric transcripts of Pax3-FKHR or Pax7-FKHR, respectively, are expressed in rhabdomyosarcomas (Shapiro et al., 1993; Davis et al., 1994).

Evidence for Pax2 expression has been achieved for Wilm's tumours of the kidney (Dressler & Douglass, 1992). Pax2 is necessary for kidney development—its expression, however, is down-regulated as early as during embryogenesis and is no longer detected in normal adult kidney (Dressler et al., 1990).

A therapeutic or diagnostic means is known from DE-A-42 25 569 which contains as an active ingredient at least one nucleic acid hybridizing to a Pax gene. Pax1 through Pax8 are mentioned as Pax genes. Furthermore, the use of such means as a molecular probe in tumour diagnosis and as antisense nucleic acid for the inhibition of gene expression are described. DE-A-42 25 569 does not mention a therapeutic or diagnostic means using a nucleic acid hybridizing to the Pax9 gene nor the uses of such means. This may be due to the fact that at the filing date of DE-A-42 25 569 (03/08/1992), the existence of the Pax9 gene was yet unknown. Further, this German Published Application does only disclose in general the use of such probes in tumour diagnosis or tumour therapy. There are no specific fields of tumour diagnosis or tumour therapy disclosed in which the agent might actually be useful, and the disclosure of which would be of importance considering the variety and heterogeneity of tumours. In particular, this Published Application does not disclose a means which may also be used in the early diagnosis of precancerogenic lesions, particularly of dysplasias of the stratified squamous epithelium.

It is an object of the present invention to provide a novel probe comprising as an active ingredient at least one nucleic acid which is useful for tumour diagnosis and tumour therapy of dysplasias, metaplasias and tumours of epithelial cells and cartilage cells.

According to the invention, this object has been solved by the therapeutic or diagnostic means characterized in more detail in claim 1. Preferred embodiments become clear from the dependent claims and the alternative independent claims.

According to the invention, it has been surprisingly found that a nucleic acid coding for the amino acids corresponding to 30 to 337 of SEQ ID No:2 and hybridizing to the Pax9 gene or a gene derived therefrom may be used in the diagnosis and therapy of dysplasias, metaplasias, and tumours of epithelial cells and cartilage cells. In particular, such nucleic acid is excellently useful in the diagnosis of squamous epithelial carcinomas. A diagnostic means of that type may be of excellent use in the early diagnosis of epithelial dysplasias, metaplasias, and tumours of the stratified squamous epithelium. Using this, for example an early diagnosis of dysplasias as potential precursors of metaplasias and tumours of the respective tissues may be performed at a very early stage in which neither a macroscopical nor a microscopical (!) detection of pathologically altered cells can be performed.

The therapeutic or diagnostic means of the invention contains as an active ingredient at least one nucleic acid comprising (a) a nucleic acid sequence coding for Pax9 protein, (b) a portion thereof, (c) a nucleic acid sequence hybridizing to the nucleic acid sequences of (a) and/or (b) under stringent conditions, or (d) a nucleic acid sequence being complementary to the nucleic acid sequences of (a), (b), and/or (c).

In a further embodiment of the invention, the nucleic acid comprises the sequence coding for amino acids 1–208 and the sequence coding for amino acids 209–341 (see SEQ ID No:2; FIG. 1B).

Due to the cloning technique used, it has been impossible to determine nucleotides 1–4 and 1018–1023, respectively, or the corresponding amino acids 1 and 2 and amino acids 340 and 341, respectively. In the accompanying FIG. 1B, these amino acids have been designated by "*". In contrast, the sequence protocol starts with nucleotide 5 (designated 1) which has actually been sequenced.

The nucleic acid may be a DNA or a RNA which are optionally modified.

Preferably, the nucleic acid of the invention hybridizes to the Pax9 gene under stringent conditions. According to the invention, stringent conditions are defined as conditions allowing for selective and detectable specific binding of the nucleic acid to a Pax9 gene or a derivative thereof, or a Pax9 transcript or a derivative thereof. Preferably, such hybridization under stringent conditions is defined as a hybridization at 42° C. in 50% formamide and subsequent washing of the filter at 65° C. in an aqueous solution after which still binding of the probe to the Pax9 gene or the Pax9 RNA or derivatives thereof may be detected. If shorter nucleic acids are used as probes, however, it may be necessary to employ less drastic hybridization and/or washing conditions. Highly stringent conditions consist of: washing of the filter in 0.1×SSC, 0.1% SDS at 68° C.

To specifically detect the Pax9 gene, a nucleic acid sequence must be used which is derived from the non-conserved region of the gene and preferably the region not encoding the paired domain. The same applies if the Pax9 gene is to be blocked.

The agent of the invention may be used in an efficient amount as a molecular probe in the diagnosis or therapy of dysplasias, metaplasias, and tumours. Further, it may be used as an antisense nucleic acid for the specific inhibition of Pax9 gene expression.

Furthermore, according to the invention there is provided a method for tumour diagnosis and a method for the inhibition of the Pax9 gene expression employing the agent of the invention in an effective amount.

A further therapeutic or diagnostic means provided according to the invention contains at least one active ingredient in an effective amount comprising at least one Pax9 protein, analogues, portions, conjugates, oligomers, and/or mixtures thereof. Such means will be used in an effective amount in the diagnosis and/or therapy of dysplasias, metaplasias, and tumours of epithelial cells.

In a further embodiment of the invention, there is provided a therapeutic or diagnostic means containing at least one active ingredient comprising at least one antibody against a Pax9 protein, analogues, portions, conjugates, oligomers, and/or mixtures thereof.

The therapeutic and diagnostic means provided according to the invention containing a portion of the Pax9 protein, analogues, conjugates, oligomers, and/or mixtures thereof preferably contains amino acids 132–341, and in a further preferred embodiment contains amino acids 251–341, each shown in FIG. 1B (this method of counting also includes the amino acids not covered by the sequencing technique used; if those are not considered in the counting, one obtains amino acids 130–337 and 249–337, respectively), or amino acids 130–337 or 249–337 according to SEQ ID No:2.

In a further preferred embodiment of the invention, the therapeutic or diagnostic means provided by the invention has at least one active ingredient comprising at least an antibody, preferably a monoclonal antibody against a Pax9 protein, analogues, portions, conjugates, oligomers, and/or mixtures thereof, wherein in specific embodiments of the invention those antibodies may be directed against epitopes localized in regions 132–341 or 251–341, respectively, of the amino acid sequence of FIG. 1B, or 130–337 or 249–337 according to SEQ ID No: 2.

The invention further provides the Pax9 protein with the amino acid sequence according to SEQ ID No: 2, analogues, portions, conjugates, oligomers and/or mixtures thereof.

Nucleotide sequence 1–627 and amino acid sequence 1–208 (SEQ ID No: 2) are already described in Stapleton (1993), and in a specific embodiment, these are not encompassed by the scope of the invention.

The present invention is also directed to a DNA coding for the above-mentioned Pax9 protein, and a RNA derived from said DNA.

The antibodies of the invention are preferably monoclonal antibodies available according to the method of Köhler and Milstein in a well-known manner by immunization of a test animal, preferably a mouse, with the Pax9 protein or/and a mixture of Pax9 proteins, preparation of antibody-producing B cells or of spleen cells from the immunized test animal followed by fusion of the antibody-producing cells to a suitable leukemia cell for the generation of hybridomas.

Preferably, the antibodies of the invention may be used in vitro and/or in vivo as means for tumour diagnosis and/or tumour therapy. In this case, the antibodies may also be employed in the form of fragments (e.g. Fab or F(ab)$_2$ fragments) and optionally coupled to a detectable group (enzyme, fluorescent marker, radioactive marker, nuclear resonance marker etc.) or to a toxin (e.g. ricine, diphtheria toxin etc.). The preparation of such antibody derivatives is carried out in a way which is well-known to the skilled artisan in the field of immunology (such as by covalent coupling via a bi-functional linker). The invention also comprises antibodies, in particular monoclonal antibodies directed against a Pax9 protein, analogues, portions, conjugates, oligomers and/or mixtures thereof. These antibodies may be employed in the methods provided according to the invention as well as in the uses claimed.

The therapeutic or diagnostic means provided by the invention are used for diagnosis or therapy of dysplasias, metaplasias, and tumors of epithelial cells, preferably of the stratified squamous epithelium, and of cartilage cells. The diagnosis and therapy of alterations in oesophagus, skin, such as psoriasis, buccal mucosa, tongue, cornea, vagina, cervix, endometrium, anus, sebaceous glands of the skin, and cartilage represent preferred fields of the invention. In particular, a potential field of the present invention is the early diagnosis of epithelial cell dysplasias.

Diagnosis and in particular early diagnosis, as well as therapy in the case of metaplasias is an important field of the present invention. A metaplasia, and thus, in this case the conversion of an epithelium into a stratified squamous epithelium may theoretically occur at every site of the body where "non-squamous epithelia" are present. It is for example well-known that the simple squamous epithelium of the trachea of smokers is frequently converted into a stratified squamous epithelium. Another important example is the conversion of the endometrial epithelium (generally a monolayer) into a stratified squamous epithelium. These sites obviously show an increased risk for the development of a squamous epithelial carcinoma. The stratified squamous epithelia can be diagnosed and treated by the agent provided by the invention which contains at least one active ingredient having at least one nucleic acid hybridizing to a Pax9 gene or a derivative thereof.

As detailed in the following, it could be demonstrated according to the invention that higher amounts of the Pax9 protein are localized in the cytoplasm in epithelial cell dysplasias than in normal cells. Therefore, according to the invention, recombinant vectors may be used having a sequence coding for a Pax9 protein, an analogue, portions, conjugates, oligomers, and mixtures thereof, being in a preferred embodiment operably linked to one or more signal sequences for the directed transport of the Pax9 protein into the cell nucleus. This vector may for example be derived from a plasmid or a viral vector. Typical vectors well-known or still to be developed in the field of gene therapy may be used according to the invention. Preferably, this vector is an expression vector which may be expressed in procaryotic as well as in eucaryotic cells.

The present invention also comprises eucaryotic cells and procaryotic cells transformed by a vector containing the Pax9 gene of the invention.

The vectors containing the Pax9 gene according to the invention are useful in somatic gene therapy of humans. For example, they may be used for terminal differentiation of tumour cells and tumour precursor cells.

Also comprised by the invention are analytic kits for the analysis of Pax9 expression in cartilage as well as epithelial cells, and in particular in cells of the squamous epithelium with respect to dysplasias, metaplasias, and tumours.

BRIEF DESCRIPTION OF THE FIGURES

In the following, the invention will be explained with regard to the accompanying Figures. The Figures show:

FIG. 1A: the amino acid sequence of the human Pax9 gene having 341 amino acids (SEQ ID NO:2).

FIG. 1B: a comparison of the amino acid sequence of the human Pax9 gene (HUPax9) (SEQ ID NO:2) to that of the mouse (MPax9)(SEQ ID NO:5).

Figure 2:
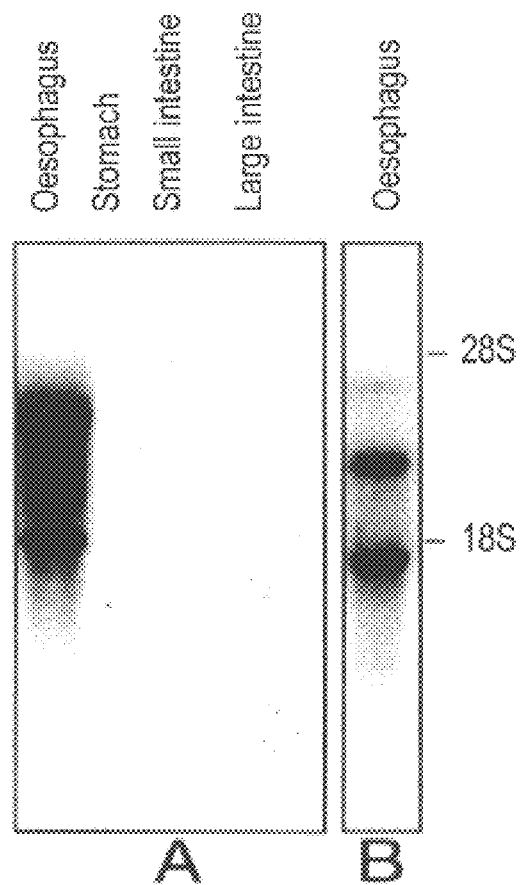
FIG. 2: Northern blot analysis of Pax9 expression in the oesophagus, stomach, small intestine and large intestine (FIG. 2A), and in human oesophagus (FIG. 2B).

The size of the size standards shown in the Figures in each case is 100 μm.

In the following, the invention will be explained in more detail with respect to the Examples. It will be understood that the invention is not limited to the specific Examples mentioned but that the skilled artisan in the field of molecular biology will be able to develop further embodiments in a well-known manner.

The Pax9 Gene

Evidence for the existence of the Pax9 gene has been achieved for the genomes of mouse (Wallin et al., 1993), humans (Stapleton et al., 1993), and chicken (Peters et al., 1995). The amino acid sequence of the DNA-binding "paired" domain is identical in these organisms. The amino acid sequences of the human (combined from Stapleton et al., 1994, and Peters et al., unpublished) and murine Pax9 proteins (Neubuser et al., 1995) are shown in FIG. 1. The "paired" domain and another conserved sequence motive consisting of 8 amino acids, the octapeptide, are boxed in this FIG.

Besides other domains of expression, during the embryogenesis of mouse and chicken Pax9 is expressed in the epithelium of the undifferentiated pharynx (Neubüser et al., 1995; Peters et al., 1995). In the further course of embryogenesis, the pharyngeal epithelium i.a. contributes to the organogenesis of the oesophagus. During this, the epithelium being originally a simple squamous epithelium is developed into a stratified squamous epithelium which in the adult organism lines the complete oesophagus. It is well-known that Pax9 is expressed in the stratified squamous epithelium of the oesophagus of chicken (Peters et al., 1995), mouse, and of humans (Peters et al., unpublished). Stratified squamous epithelia may also be found in skin, buccal mucosa, tongue, cornea, vagina, and anus of the human organism. The sebaceous glands of the skin represent a similar structure made of epithelial cells. With the cornea being the only exception, the expression of Pax9 could be demonstrated according to the invention in all of the above-mentioned organs of the adult mouse. In the late phase of mouse embryogenesis, Pax9 is also expressed in a specific phase of cartilage differentiation (Peters and Balling, unpublished). In this phase, the cells expressing Pax9 mark the intermediate phase between the proliferating columnar cartilage and the layer of differentiating bullous cartilage which in the further course of development becomes enchondrally ossified. Analogously to the expression in stratified squamous epithelia, Pax9 is expressed also in the cartilage cells not by the proliferating but by the differentiating cells. Therefore, the present invention which followed from the experiments described below may be applied to these organs as well.

Results

The present invention is based on the analysis of the Pax9 gene and protein expression in the stratified squamous epithelium, in particular in normal human and murine oesophageal epithelium, as well as in cartilage cells of growing long bone during mouse embryogenesis.

1. Pax9 Gene Expression

The nucleotide sequence of the exon containing the "paired" box is the only sequence known of the human Pax9 gene to date (Stapleton et al., 1993). This study also includes the isolation of the cDNA coding for Pax9 of humans from total oesophageal RNA. Isolation of total RNA was performed using the "RNEASY TOTAL RNA" kit (Qiagen, Hilden). For this purpose, fresh section material was provided by the Institut für Pathologie of the Klinikum Rechts der Isar in Munich. 1 μg of total RNA was used to perform reverse transcription. For initiation of the reverse transcriptase (Superscript obtained from Gibco-BRL, Karlsruhe) the synthetic DNA oligonucleotide 5'-CCC AAGCTTTGGACGCTCCCATCAGAGTGC-3' (SEQ ID NO:3) (HindIII restriction site underlined) was used. This sequence was derived from the murine Pax9 cDNA (Neubüser et al., 1995), and it covers the stop codon as well as the last two carboxyterminal amino acids of the murine Pax9 protein. Amplification of the human Pax9 cDNA was carried out subsequently using the polymerase chain reaction (PCR). In addition to the DNA oligonucleotide presented above, the oligonucleotide 5'-CCC AAGCTTAGCCAGCCTTCGGGGAGGTG-3'-(SEQ ID NO:4) was used which is derived from the 5'-region of the "paired" box of the human Pax9 gene (Stapleton et al., 1993). The following conditions were employed for 25 amplification cycles: 1 min denaturation at 94° C.; 1 min oligonucleotide annealing at 60° C.; 1 min DNA polymerisation at 72° C. The DNA fragment obtained was cleaved by HindIII and cloned into the HindIII restriction site of plasmid pKS (Stratagene, Heidelberg). Sequencing was performed using the Sequenase kit according to manufacturer's instructions (USB, Cleveland, USA). The sequence of the derived amino acids and the comparison with the murine Pax9 protein are presented in FIGS. 1A and 1B, respectively.

The coding region of the murine Pax9 cDNA (Neubuser et al., 1995) and of human Pax9 cDNA (Peters et al., unpublished) were each radiolabeled (Feinberg & Vogelstein, 1984) and hybridized to membrane-bound total oesophageal RNA (Northern blot analysis). Following hybridization under highly stringent conditions (0.1×SSC, 0.1% SDS, 68° C.), by which cross-hybridization to other Pax genes is excluded, washing of the membranes (HybondN, Amersham, Braunschweig) was carried out. FIG. 2 shows the results of the Northern blot analysis. It becomes clear from FIG. 2A that Pax9 is expressed in the oesophagus in mouse whereas no transcripts are detected in glandular stomach, small intestine and large intestine. Pax9 transcripts can also be detected in human oesophagus (FIG. 2B). A comparison to the internal size standards of ribosomal 28S RNA (6333 bases) and 18S RNA (2366 bases), respectively, revealed that the transcripts of the human Pax9 gene are about 5.3 kilobases (upper band), 3.5 kilobases (median band), and 2.1 kilobases (lower band) in length.

2. Detection of Pax9 Proteins

It was examined whether the Pax9 transcripts are translated and are detectable as Pax9 proteins in oesophageal protein extracts. For this purpose, polyclonal antibodies directed against the Pax9 protein were generated in rabbits. To perform this, the cDNA sequence coding for amino acids 252–342 of the murine Pax9 protein (Neubüser et al., 1995)

was cloned into vector pMAL™-c2 (New England Biolabs). The resulting plasmid, pMALP9, codes for a fusion protein consisting of a 42.7 kd maltose-binding *E. coli*-derived protein (Guan et al., 1987) and the carboxy terminal region of the Pax9 protein. Expression and purification of the fusion protein were carried out according to manufacturer's instructions (New England Biolabs). Two rabbits were immunized subcutaneously each with 400 µg of the fusion protein in Freund's adjuvant. Further immunization was performed in intervals of four weeks in each case using 100 µg of fusion protein. For all examinations, immune serum of one of the rabbits designated 281-IV and obtained after either the third or the fourth immunization was used. A second immune serum, designated 105-IV, recognizing the "paired" domain of the Pax9 protein (Peters et al., 1995) was used to confirm the specificity of immune serum 281-IV.

Figure 3:
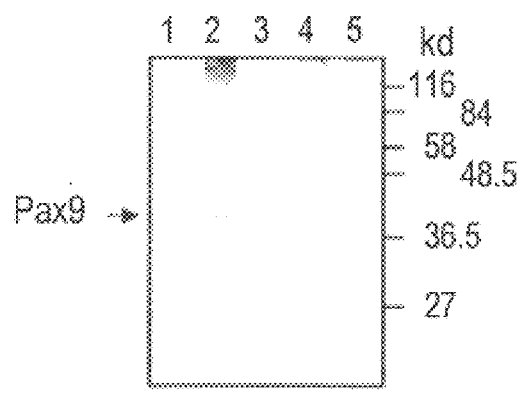
FIG. 3: the detection of the Pax9 protein in protein extracts of murine and human oesophagus (Western blot analysis).

For detection of Pax9 proteins, the protein extracts from human or murine oesophagus, respectively, were prepared according to well-known protocols (Peters et al., 1995), 50 µg of each of the protein extracts were separated on 12% polyacrylamide gels (Laemmli, 1970), and were subsequently transferred by semi-dry electroblotting onto Fluorotrans membranes (Pall, Dreieich). To evaluate protein sizes, a protein size standard (Sigma, Munich) was included. The membranes were blocked by overnight incubation in phosphate-buffered saline (=PBS) containing 3% bovine serum albumine, 5% normal sheep serum, and 5% low fat milk powder. Subsequently, the immune serum was added in a dilution of 1:200 and incubated for one hour at 21° C., followed by washing of the membrane in 0.1k Tween 20 in PBS for 20 minutes, and afterwards another incubation was performed with an anti-rabbit IgG and alkaline phosphatase conjugate (Boehringer, Mannheim) in a dilution of 1:2000. Detection of protein bands was carried out using the color substrates 4-nitro blue tetrazolium HCl (NBT) and 5-bromo-4-chloro-3-indolyl phosphate (X-phosphate) according to manufacturer's instructions (Boehringer, Mannheim). FIG. 3 shows the result of this Western blot analysis.

Immune serum 281-IV is able to detect in the protein extract of murine oesophagus a protein with an apparent molecular weight of about 39 kd (FIG. 3, lane 1). This size corresponds to the molecular weight of the Pax9 protein to be derived from the amino acid sequence (39 kd, cf. FIG. 1). This result is confirmed using the second immune serum (105-IV) which recognizes the Pax9 paired domain and detects a band having the same size (FIG. 3, lane 2). Immune serum 105-IV shows cross-reaction to the human Pax9 protein and is also able to detect in the protein extract from human oesophagus a protein having a molecular weight of about 39 kd (FIG. 3, lane 3). Lanes 4 (protein extract from murine oesophagus) and 5 (protein extract from human oesophagus) of FIG. 3 represent the results of control incubations with normal rabbit serum and prove the specificity of immune sera 281-IV and 105-IV.

3. Localization of the Pax9 Protein in Normal Oesophageal Epithelium of Mouse and Man The subcellular localization of Pax9 proteins in normal oesophageal epithelium of mouse, man, and in cartilage of the murine embryo was examined using immunohistochemical methods. The same polyclonal antibodies as described under point 2. were used in these experiments. Paraffin sections having a thickness of 5–7 µm of formalin-fixed tissue were deparaffinized twice for 10 min in xylol, 5 min in isopropanol, 2 min in each of 100%/96%/90%/70%, and 50% ethanol, and were afterwards equilibrated for 5 min in PBS. If incubations with antibody 105-IV were carried out, the sections were pretreated for 10 min in 10 mM citric acid (pH 6.0) and boiled in a microwave oven. Then, the sections were incubated for 90 min at 37° C. in the antibody dilutions of immune serum 281-IV or in pre-immune serum (1:200 in PBS, 3% BSA), or 105-IV (1:200 in PBS, 3% BSA, 15% normal sheep serum), respectively. (1) Sections of murine tissue were subsequently treated as follows: After washing for 5 min in PBS the sections were incubated with an anti-rabbit IgG and alkaline phosphatase conjugate (diluted 1:200 in PBS, 3% BSA) (Boehringer, Mannheim). The color reaction was performed according to manufacturer's instructions (Boehringer, Mannheim) using substrates 4-nitro blue tetrazolium HCl (NBT) and 5-bromo-4-chloro-3-indolyl phosphate (X-phosphate) forming a purplish-blue precipitate. Endogenous alkaline phosphatase activity was blocked by addition of levamisole (Sigma, Munich) (final concentration of 5 mM) to the staining solution. (2) Sections of human tissue were further treated as follows: After washing for 5 min in PBS, the sections were incubated with mouse-anti-rabbit IgG (Dianova, Hamburg) diluted 1:200 in PBS (containing 20% of human serum) for 30 min at 21° C. After a further washing in PBS the sections were incubated with rabbit-anti-mouse IgG (Dakopatts, Denmark) diluted 1:50 in PBS (containing 20% human serum) for 30 min at 21° C. Afterwards, they were washed again in PBS followed by incubation with an APAAP complex (Dakopatts, Denmark) diluted 1:50 in PBS for 30 min at 21° C. The color reaction was performed using substrates naphthol-AS-MX phosphate (Sigma, Munich) and Fast Red (Serva, Heidelberg) forming a red precipitate. Endogenous alkaline phosphatase activity was blocked by addition of levamisole (5 mM) to the staining solution. Following the immunohisto-chemical staining, sections of human tissue samples were stained for 10 sec by hemalum leaving the cell nuclei with a slight blueish stain.

For microscopy, cover slip preparations of the sections were prepared in glycerine/gelatin (Merck, Darmstadt). The documentation was performed using Kodak Ektachrome slide film and a Leitz Axioplan microscope with Normarski optics. For the visualization of histology, sections of analogous regions were deparaffinized as described above and stained by hematoxylin/eosin.

The stratified squamous epithelium of human oesophagus (FIG. 4E) is composed of a stem cell-containing basal cell layer (Bz) with mitotic activity and of the suprabasal cell layers (Sz) which arise from the basal layer and build up the non-keratinized stratified squamous epithelium as a result of specific differentiation. The mouse exhibits a similar structure of the squamous epithelium, however, in contrast to human squamous epithelium the murine epithelium is keratinized (FIG. 4A).

A detailed study of the Pax9 gene expression was first performed on squamous epithelium from murine oesophagus. Adult CD1-strain mice were used which had been breeded in the GSF in-house animal station. The result of this examination was that Pax9 is expressed in the suprabasal cell layers but not in the mitotically active basal layer. FIG. 4B (incubation with 281-IV) and 4C (incubation with 105-IV) represent examples of the results of immunohistochemical experiments. Both immune sera are able to detect the Pax9 protein in cells of the suprabasal cell layers in which differentiation of the epithelial cells occurs. The localization of the Pax9 protein in the cell nuclei is in accordance with its properties as a transcription factor. The result of the control incubation using normal rabbit serum (FIG. 4D) shows unspecific background staining mainly in the keratinous layer (K). This finding suggests that in the normal organism Pax9 may be involved in the differentiation of the oesophageal epithelium but may not directly influence its proliferation which takes place in the basal cell layer. On the other hand, it is well-known that the mitotic activity of the stem cells follows a circadian rhythmicity and in mice is highest during the night (Scheving et al., 1979). Thus, it was examined whether a daytime-dependent Pax9 expression could be detected in the basal layer cells having mitotic activity. For this purpose, adult mice were kept under constant light conditions (12 h light/12 h darkness). For a period of 24 h, the oesophagus of in each case three mice was prepared in intervals of three hours, fixed and examined immunohistochemically according to the technique described above. In none of the total of 24 independent tissue samples Pax9 protein could be detected in the basal cell layer (not shown). The expression pattern in all cases corresponds to the one shown in FIG. 4B or 4C, respectively.

For immunohistochemical examinations of human oesophageal epithelium paraffin sections were prepared from the collection of the Institut fur Pathologie (Klinikum Rechts der Isar, Munich).

Figure 4:
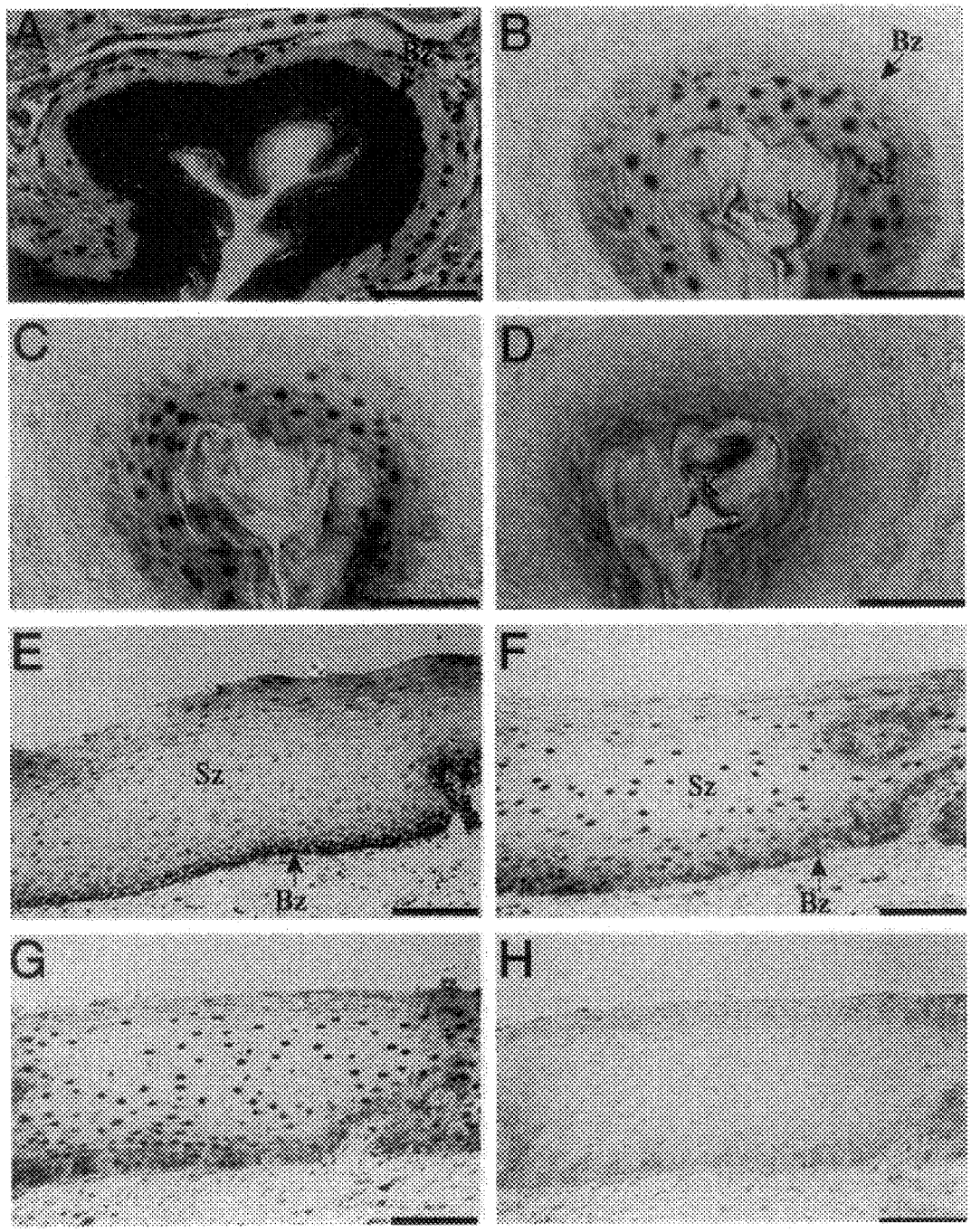
FIG. 4A: localization of Pax9 in keratinized murine squamous epithelium.
FIG. 4B: immunohistochemical staining of murine oesophagus epilethium with polyclonal antibody 281-IV.
FIG. 4C: immunohistochemical staining of murine oesophagus epilethium with polyclonal antibody 105-IV.
FIG. 4D: control incubation with normal rabbit serum in oesophagus epithelium of the mouse.
FIG. 4E: localization of Pax9 in normal human oesophagus epithelium.
FIG. 4F: localization of Pax9 in normal human oesophagus epithelium in the cell nucleus.
FIG. 4G: localization of Pax9 in normal human oesophagus epithelium in the cell nucleus.
FIG. 4H: control staining with normal rabbit serum.

Also in normal human oesophageal epithelium, the Pax9 protein is localized in the cell nuclei of the suprabasal cell layer (FIGS. 4F and 4G). In the control incubation with normal rabbit serum no specific staining is observed (FIG. 4H).

In normal oesophageal epithelium, the Pax9 protein is localized in the cell nuclei of the suprabasal layers. This localization corresponds to a terminal differentiation of these cells.

Figure 5:
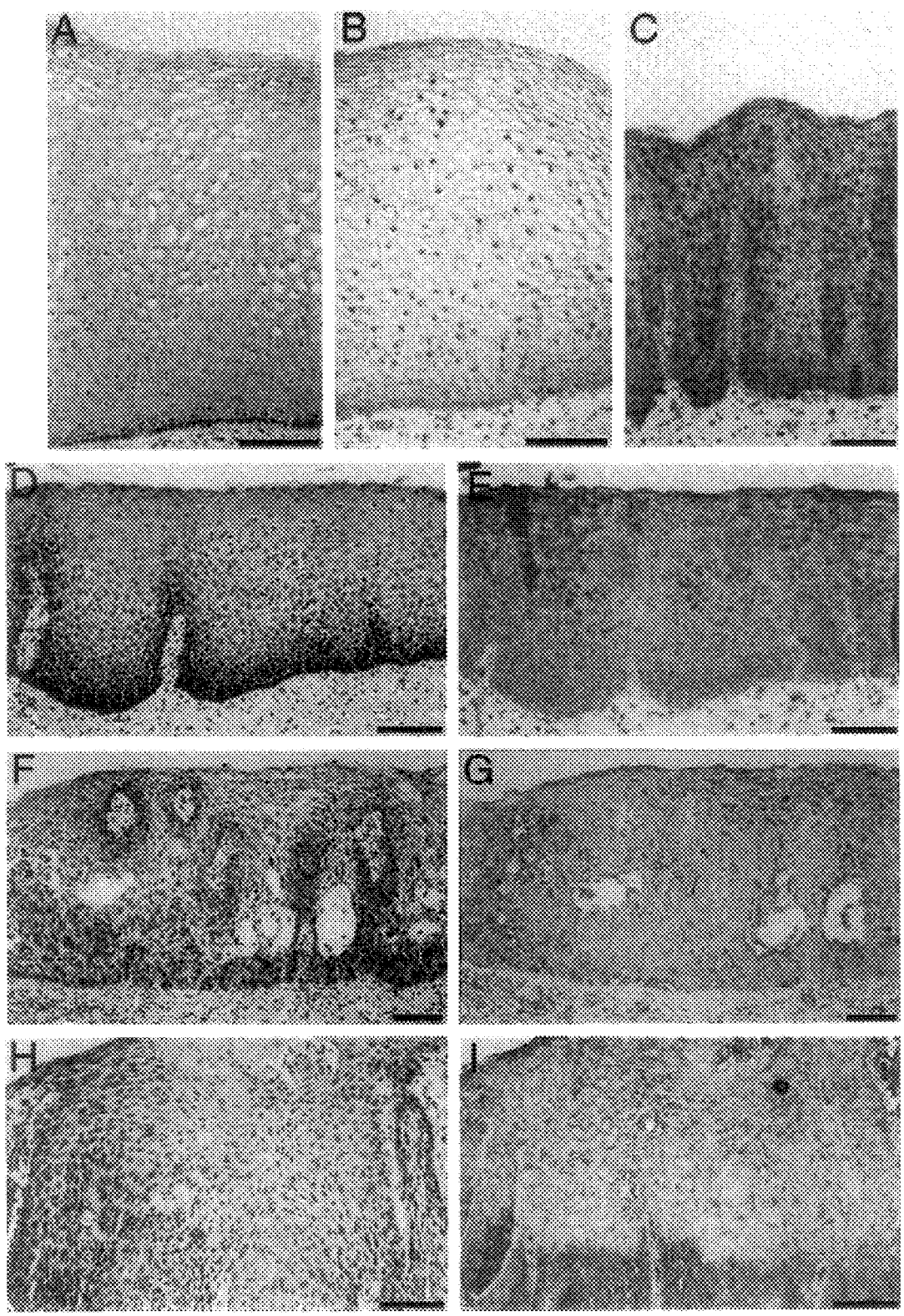
FIG. 5A: localization of Pax9 in human leukoplasia, oesophagus tissue.
FIG. 5B: localization of Pax9 in human leukoplasia, oesophagus tissue.
FIG. 5C: distribution of Pax9 protein in another region of the oesophagus tissue sample of FIG. 5B.
FIG. 5D: Pax9-localization in dysplasias of human mucosal epithelium, oesophagus tissue.
FIG. 5E: Pax9-localization in dysplasias of human mucosal epithelium, oesophagus tissue.
FIG. 5F: Pax9-distribution in a human severe dysplasia-oesophagus tissue.
FIG. 5G: Pax9-distribution in the cytoplasm of the oesophagus tissue sample of FIG. 5E.
FIG. 5H: Pax9-distribution in a human epithelial carcinoma, oesophagus tissue.
FIG. 5I: absence of nuclear localization of Pax9-protein in human epithelial carcinoma, oesophagus tissue.
Figure 6:
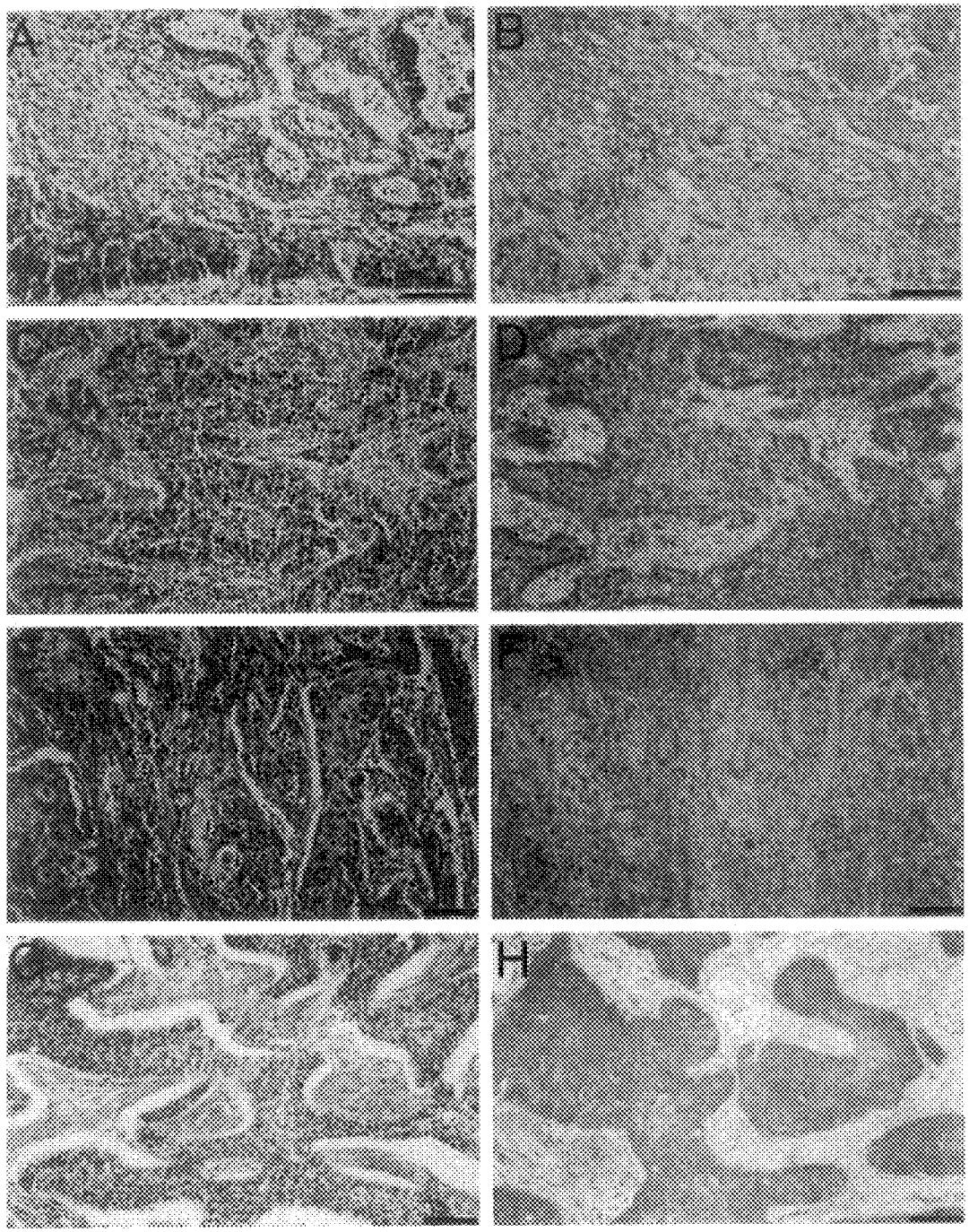
FIG. 6A: Pax9-distribution of human squamous epithelial carcinoma, buccal mucosa.
FIGS. 6C, 6E, and 6G: different invasively growing squamous epithelial carcinomas of the G2 type and their Pax9-protein distribution (6C-oesophagus, 6E-oesophagus, 6G-lung).
FIGS. 6D, 6F, and 6H: Pax9-protein distribution in squamous epithelial carcinomas of the G2 type (6D-oesophagus, 6F-oesophagus, 6H-lung).

4. Localization of the Pax9 Protein in Pathologically Altered Stratified Squamous Epithelia and in Squamous Epithelial Carcinomas of Humans Leucoplasias presenting themselves as whitish focal thickenings of the mucosal epithelium are believed to be precancerogenic stages. However, in most of the cases the polarity and differentiation of the epithelium is maintained (FIG. 5A) and is similar to that of normal oesophageal epithelium (see FIG. 4E). FIG. 5B shows the localization of the Pax9 protein in a leucoplasia. Similar to normal oesophageal epithelium Pax9 protein is localized in the cell nuclei of the suprabasal layers. FIG. 5C represents the distribution of Pax9 protein in another region of the same tissue sample. Although in this case the protein is also predominantly localized in the cell nuclei, an additional distinct red staining is observed in the cytoplasm. In contrast, in dysplasias of the mucosal epithelium the Pax9 protein distribution becomes drastically altered. Surprisingly, already in mild dysplasias of the mucosal epithelium (FIG. 5D) the Pax9 protein can no longer be detected in the cell nuclei of the suprabasal layers (FIG. 5E). In this tissue sample and also in an example of a severe dysplasia (FIG. 5F) the Pax9 protein is predominantly localized in the cytoplasm (FIG. 5G). FIGS. 5H and 6A each show an histological in situ stain of a carcinoma. These tumours develop intraepithelially and fail to exhibit invasive growth into the underlying mesenchyme. As in the dysplasias shown, also in this case the malignancy of the epithelium correlates with the absence of nuclear localization of the Pax9 protein (FIG. 5I).

Figure 7:
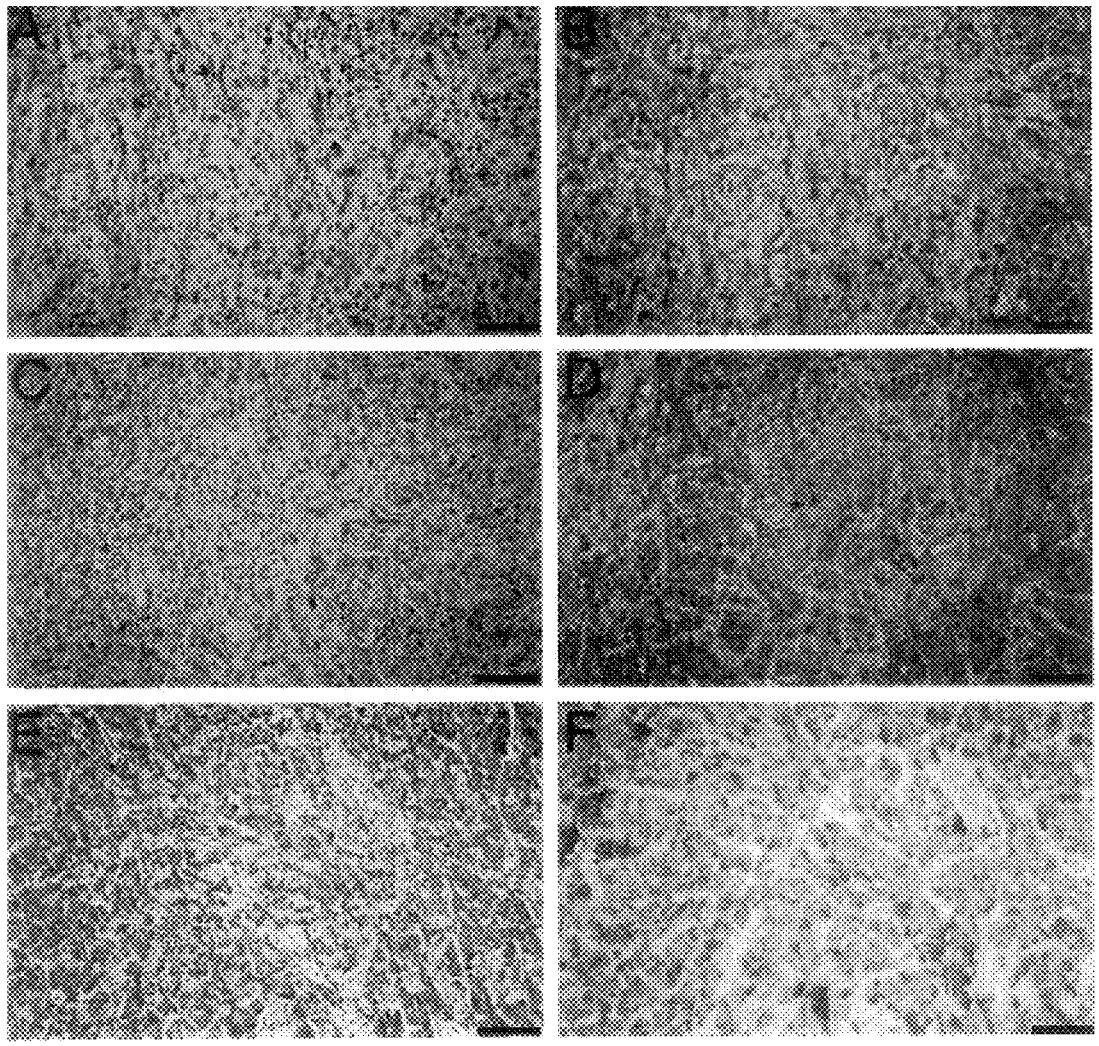
FIGS. 7A, 7C, and 7E: Pax9-distribution in different invasively growing squamous epithelial carcinomas of the G3 type (7A-buccal mucosa, 7C-buccal mucosa, 7E-oesophagus).
FIGS. 7B, 7D, and 7F: Pax9-protein distribution in squamous epithelial carcinomas of the G3 type (7B-buccal mucosa, 7D-buccal mucosa, 7F-oesophagus).

In addition, different invasively growing squamous epithelial carcinomas of the G2 type (FIGS. 6C, E, G) and G3 type (FIGS. 7A, C, E) were examined during this study. In all of the cases examined, the Pax9 protein is localized in the cytoplasm. The results are exemplified by squamous epithelial. carcinomas of the G2 type (FIGS. 6D, F, H) or the G3 type (FIGS. 7B, D, F), respectively.

The present invention provides a novel diagnostic or therapeutic means containing as an active substance at least one nucleic acid of the Pax9 gene which is particularly useful in early diagnosis of dysplasias and metaplasias of the stratified squamous epithelium as well as in tumour diagnosis and tumour therapy of squamous epithelial carcinomas. In this respect, it is of particular importance that alterations in Pax9 expression are able to indicate already precancerogenic lesions manifesting themselves as tumours only in the further course of the disease.

Figure 8:
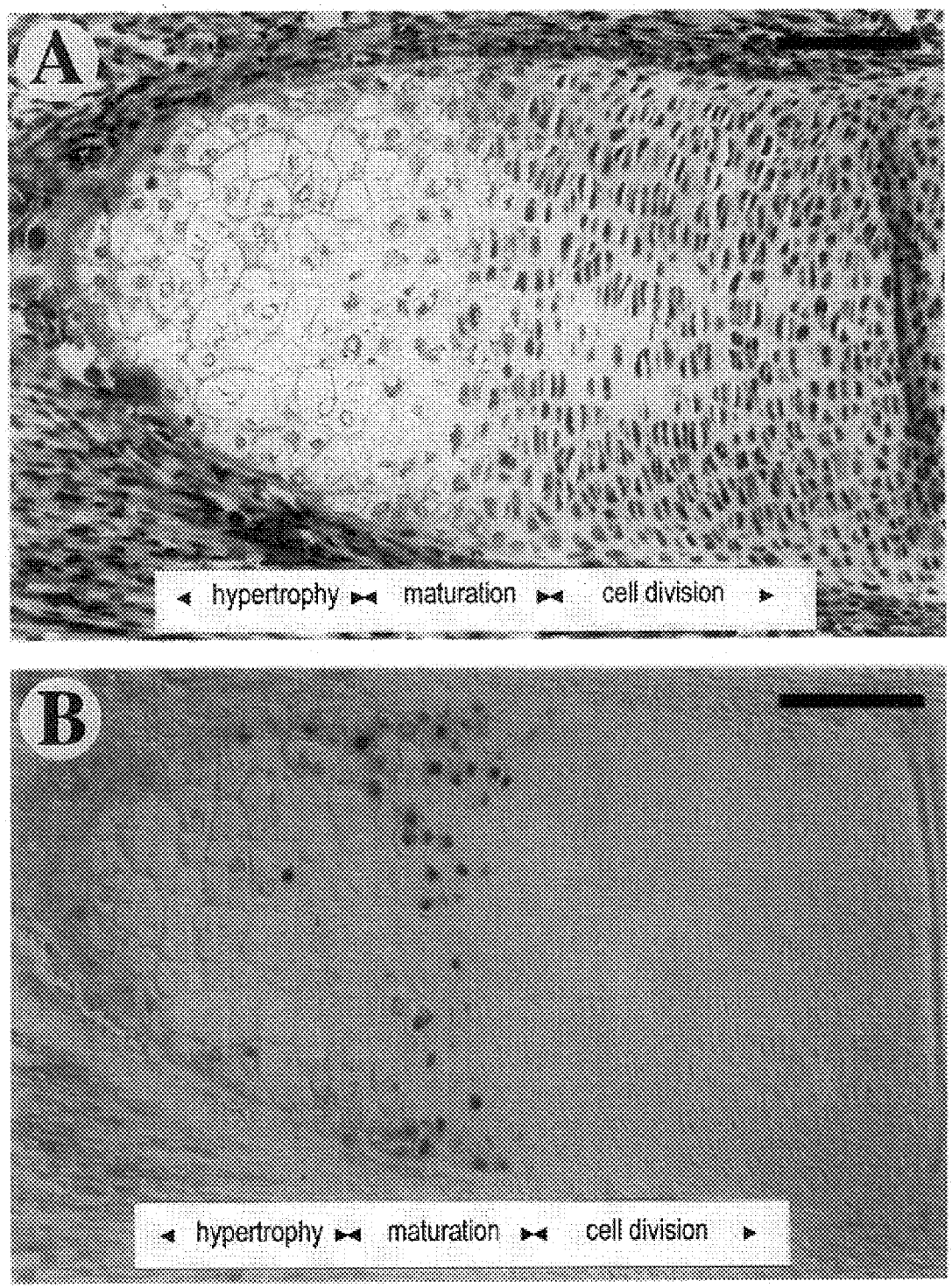
FIG. 8A: localization of Pax9-protein in columnar cartilage cells.
FIG. 8B: Pax9-protein distribution in the humerus of a 16.5 day old mouse embryo.

5. Localization of Pax9 Proteins in Cartilage Cells During Enchondral Ossification By far the largest portions of the skeleton are preformed during embryogenesis in the form of cartilaginous primordia. These primordia ossify by encondral ossification, a continuously progressing process during which the cartilage is degraded and replaced by bone substance. Simultaneously, a rapid growth of the embryonic bone must be ensured. The growth in long bone takes place in the perichondrium and at both ends of the bone, called the epiphyses. During this, dividing chondrocytes in the epiphyses are arranged to form columnar cartilage (FIG. 8A). During this phase, specific essential molecules of the extracellular matrix such as collagens II, IX, and aggrecan are expressed (Agraves et al., 1981; Bogaert et al., 1992; Nakata et al., 1993). Subsequent to the phase of cellular divisions occurs the maturation of chondrocytes which in the further course of differentiation become hypertrophic to form the bullous cartilage. During maturation, CMP (cartilage matrix protein), another specific molecule of the extracellular matrix, is expressed (Chen et al., 1995). Alterations in chondrocyte differentiation have been noted in different diseases (review in Rimoin, 1975). Herein, joint osteoarthritis is mentioned as an example. The joints of articulated bones are covered by a layer of hyaline cartilage. In the case of osteoarthritis, differentiation processes are initiated in this layer which do not occur in normal joints. Secondary cell divisions followed by chondrocyte hypertrophy are observed in the hyaline articular cartilage (Hoyland et al., 1991; van der Mark et al., 1992).

To date, no transcription factors are known which are specifically expressed during the phase of chondrocyte maturation. Surprisingly, we were able to detect Pax9, a transcription factor, in this zone. The immunohistochemical experiments performed in this study on the humerus of a 16.5 day old mouse embryo have shown that on a molecular level Pax9 exactly marks the zone of maturation which is localized between the phases of cell division and that of hypertrophy (FIG. 8B). A similar expression pattern was observed in other skeletal elements (scapula, vertebral body, digit). Analogously to the findings made in normal oesophageal epithelium, the Pax9 protein is localized in the cell nuclei. Moreover, there is obviously a further correlation between Pax9 expression in maturating bone on the one hand and Pax9 expression in the stratified squamous epithelium on the other hand: in both tissues Pax9 is expressed not by the dividing but by the differentiating cells. Therefore, besides being a marker for stratified squamous epithelia, the nuclear localization of Pax9 is also useful as a marker for cartilage cells in the phase of terminal differentiation.

In the following there are summarized!preferred embodiments of the invention:

A protein having the activity of human Pax9 and the amino acid sequence of SEQ ID No: 1, analogues, portions, conjugates, oligomers, and mixtures thereof, with the exception of a polypeptide consisting of amino acid sequence 1–208 alone or portions thereof.

A polypeptide having amino acid sequence No. 209–337 according to SEQ ID No: 1 of the human Pax9 gene or a partial sequence thereof having a function identical to that of a partial human Pax9 gene consisting of amino acids No. 209–337 according to SEQ ID No: 1.

A polypeptide having amino acid sequence No. 249–337 according to SEQ ID No: 1 of the human Pax9 gene.

A DNA coding for one of the polypeptides described above wherein said DNA may optionally be modified.

A RNA derived from said DNA wherein the RNA may optionally be modified.

A DNA which hybridizes to the above DNA under stringent conditions, and a peptide derived thereof.

Monoclonal or polyclonal antibodies directed against an epitope of the above described polypeptides.

A recombinant vector bearing a DNA sequence of the invention optionally operably linked to one or more signal sequences for the directed transport of the polypeptide into the cell nucleus.

Preferably, the vector is a plasmid or a viral vector, further preferred is an expression vector which preferably may be expressed in eucaryotic cells.

The use of a nucleic acid having (a) a nucleic acid sequence coding for amino acid sequence No. 130–337 according to SEQ ID No: 1, or a portion thereof, (b) a nucleic acid sequence hybridizing under stringent conditions to a nucleic acid sequence as under (a), or (c) a nucleic acid sequence complementary to a nucleic acid sequence as under (a) and/or (b), or a polypeptide having amino acid sequence No. 130–337 according to SEQ ID No: 1 or a portion thereof, or a polyclonal or monoclonal antibody directed against this sequence for the diagnosis or therapy of dysplasias, metaplasias, and tumours of epithelial cells and cartilage cells.

Preferably, the sequence comprises amino acids No. 209–337 or 249–337 or 130–193 or 202–337, or a portion thereof having an identical function according to SEQ ID No: 1.

The use is for diagnosis and therapy of alterations of epithelial cells of the oesophagus,-skin, buccal mucosa, tongue, cornea, vagina, cervix, endometrium, anus, and sebaceous glands of the skin as well as the cartilage, for example for diagnosis and therapy of dysplasias of the stratified squamous epithelium.

The nucleic acid of the invention may be employed as antisense nucleic acid to inhibit gene expression.

The vector according to the invention may be used in somatic gene therapy.

A process for the detection of tumours, metaplasias, and dysplasias of epithelial and cartilage cells in vitro wherein a nucleic acid having (a) a nucleic acid sequence coding for amino acid sequence No. 130–337 according to SEQ ID No: 1, or a portion thereof, (b) a nucleic acid sequence hybridizing under stringent conditions to a nucleic acid sequence as under (a), or (c) a nucleic acid sequence complementary to a nucleic acid sequence as under (a) and/or (b), or a polyclonal or monoclonal antibody directed against a polypeptide having amino acid sequence No. 130–337 according to SEQ ID No: 1 is contacted with a tissue sample containing the epithelial cells or cartilage cells to be analysed to analyse the amount and/or the localization of expression of the human Pax9 protein.

Preferably, the sequence comprises amino acids No. 209–337 or 249–337 or 130–193 or 202–337 according to SEQ ID No: 1.

The vector according to the invention may be used for terminal differentiation of tumour cells or tumour precursor cells.

The polypeptide of the invention or the nucleic acid of the invention may be employed in an analytic kit for the analysis of Pax9 expression in epithelial and cartilage cells with respect to dysplasias, metaplasias, and tumours.

A eucaryotic or procaryotic cell transformed by a vector according to the invention.

A diagnostic or therapeutic means containing at least one nucleic acid or polypeptide according to the invention.

A diagnostic means designed to be an analytic kit for the diagnosis of Pax9 expression in epithelial cells and cartilage cells with respect to dysplasias, metaplasias, and tumours.

A cDNA corresponding to the RNA provided by the invention.

The use of the sequences provided by the invention as markers for cartilage cells or for the localization and quantification of Pax9 expression in an eucaryotic cell.

A monoclonal antibody directed against an epitope of a polypeptide consisting of amino acids 130–193, 202–337, 202–248, or 249–337 (according to SEQ ID No: 1).

The above mentioned nucleic acid sequences (DNA or RNA sequences), amino acid sequences, and monoclonal and polyclonal antibodies directed against these sequences are derived from the non-conserved regions of the Pax9 gene, i.e. from the regions outside of the regions boxed in the accompanying FIG. 1B, preferably from the regions of amino acids 130–193, 202–337, 202–248, and 249–337, as well as such parts of these sequences which may be used for the use provided by the invention and the method according to the invention.

With respect to the present Specification and the Examples, the skilled artisan in the field of gene technology will be able to practice the invention in its entire scope which has been described and claimed without need for an inventive step.

References

Argraves, W. S., McKeown-Longo, P. J. and Goetnick, P. F. (1981): Absence of proteogycans core protein in the cartilage mutant nanomelia. FEBS Lett. 131, 265–268

Balling, R., Deutsch, U. & Gruss, P. (1988): undulated, a mutation affecting the development of the mouse skeleton, has a point mutation in the paired box of Pax 1. Cell 55, 531–535

Bogaert, R., Tiller, G. E., Weis, M. A., Gruber, H. E., Rimoin, D. L., Cohn, D. H. and Eyre, D. R. (1992): An amino acid substitution (Gly853-Glu) in the collagen al(II) chain produces hypochondrogenesis. J.Biol.Chem. 267, 22522–22526

Chalepakis, G., Fritsch, R., Fickenscher, H., Deutsch, U., Goulding, M. & Gruss, P. (1991): The molecular basis of the undulated/Pax-1 mutation. Cell 66, 873–884

Chen, Q., Johnson, D. M., Haudenschild, D. R. and Goetinck, P. F. (1995): Progression and recapitulation of the chondrocyte differentiation program: Cartilage matrix protein is a marker for cartilage differentiation. Dev.Biol. 172, 293–306

Davis, R. J., D'Cruz, C. M., Lovell, M. A., Biegel, J. A. & Barr, F. G. (1994): Fusion of Pax7 to FKHR by the variant t(1;13)-(p36;q14) translocation in alveolar rhabdomyosarcoma. Cancer Research 54, 2869–2872

Dressler, G., Deutsch, U., Chowdury, K., Nornes, H. O. & Gruss, P. (1990): Pax-2, a new murine paired-box-containing gene and its expression in the developing excretory system. Development 109, 787–795

Dressler, G. & Douglass, E. C. (1992): Pax-2 is a DNA-binding protein expressed in embryonic kidney and Wilms tumor. Proc.Natl.Acad.Sci.USA 89, 1179–1183

Epstein, D. J., Vekemans, M. & Gros, P. (1991): splotch (Sp2H), a mutation affecting development of the mouse neural tube, shows a deletion within the paired homeodomain of Pax-3. Cell 67, 767–774

Feinberg, A. P. & Vogelstein, B. (1984): A technique for radiolabeling DNA restriction endonuclease fragments to high specific activity. Anal.Biochem. 137, 266–267

Gruss, P. & Walther, C. (1992): Pax in development. Cell 69, 719–722

Guan, C., Li, P., Riggs, P. D. & Inouye, H. (1987): Vectors that facilitate the expression and purification of foreign peptides in *Escherichia coli* by fusion to maltose-binding protein. *Gene* 67, 21–30

Halder, G., Callaerts, P. & Gehring, W. J. (1995): Induction of ectopic eyes by targeted expression of the eyeless gene in Drosophila. *Science* 267, 1788–1792

Hill, R. E., Favor, J., Hogan, B. L. M., Ton, C. C. T., Saunders, G. F., Hanson, I. M., Prosser, J., Jordan, T., Hastie, N. D. & van Heyningen, V. (1991): Mouse small eye results from mutations in a paired-like homeobox-containing gene. *Nature* 354, 522–525

Hoyland, J. A., Thomas, J. T., Donn, R., Marriott, A., Ayad, S., Boot-Handfort, R. P., Grant, M. E. and Freemont, A. J. (1991): Distribution of type X collagen mRNA in normal and osteoarthritic human cartilage. *Bone Miner.* 15, 151–164

Kozmik, Z., Wang, S., Döfler, P., Adams, B. & Busslinger, M. (1992): The promoter of the CD19 gene is a target for the B-cell-specific transcription factor BSAP. *Mol.Cell.Biol.* 12, 2662–2672

Laemmli, U. K. (1970): Cleavage of structural proteins during the assembly of the head of bacteriophage T4. *Nature* 227: 680–685

Maulbecker, C. C. & Gruss, P. (1993): The oncogenic potential of Pax-genes. *EMBO J.* 12, 2361–2367

Nakata, K., Ono,K., Miyazaki, J., Olsen, B. R., Muragaki, Y., Adachi,m E., Yamamura, K. and Kimura, T. (1993): Osteoarthritis associated with mild chondrodysplasia in transgenic mice expressing al(IX) collagen chains with a central deletion. *Proc.Natl.Acad.Sci.USA* 90, 2870–2874

Neubüser, A., Koseki, H. & Balling, R. (1995): Characterization and developmental expression of Pax9, a paired-box-containing gene related to Pax1. *Dev.Biol.* 170, 701–716

Noll, M. (1993): Evolution and role of Pax genes. *Curr.Opin.Genet.Dev.* 3, 595–605

Peters, H., Doll, U. & Niessing, J. (1995): Differential expression of the chicken Pax-1 and Pax-9 gene: In situ hybridization and immunhistochemical analysis. *Dev.Dyn.* 203: 1–16

Peterson, G. L. (1983): Determination of total protein. *Methods Enzymol.* 91: 95–119

Rimoin, D. L. (1975): The chondrodystrophies. Advances in Human Genetics 5, 1–118

Shapiro, D. N., Sublett, J. E., Li, B., Downing, J. R. & Naeve, C. W. (1993): Fusion of Pax3 to a member of the forkhead family of transcription factors in human alveolar rhabdomyosarcoma. *Cancer Research* 53, 5108–5112

Scheving, L. A., Yeh, Y. C., Tsai, T. H. & Scheving, L. E. (1979): Circadian phase-dependent stimulatory effects of epidermal growth factor on deoxyribonucleic acid synthesis in the tongue, esophagus, and stomach of the adult male mouse. *Endocrinology* 105(6), 1475–1480

Schmahl, W., Knoedlseder, M., Favor, J. & Davidson, D. (1993): Defects of neuronal migration in the pathogenesis of cortical malformations are associated with small eye (Sey) in the mouse, a point mutation in the Pax-6-locus. *Acta Neuropathol.* 86, 126–135

Stapleton, P., Weith, A., Urbanek, P., Kozmik, Z. & Busslinger, M. (1993): Chromosomal localization of seven Pax genes and cloning of a novel family member, Pax-9. *Nature Genetics* 3, 292–298

Stemmermann, G., Heffelfinger, S. C., Noffsinger, A., Hui, Y. Z., Miller, M. A. & Fenoglio-Preiser, C. M. (1994): The molecular biology of esophageal and gastric cancer and their precursors: Oncogenes, tumor suppressor genes, and growth factors. *Hum.Pathol.* 25: 968–981

Tassabehji, M., Read, A. P., Newton, V. E., Harris, R., Balling, R., Gruss, P. & Strachan, T. (1992): waardenburg's syndrome patients have mutations in the human homologue of the Pax-3 paired box gene. *Nature* 355, 635–638

Ton, C. C. T., Hirvonen, H., Miwa, H., Weil, M. M., Monaghan, P., Jordan, T., Van Heyningen, V., Hastie, N. D., Meijers-Heijboer, H. & Drechsler, M., Royer-Pokora, B., Collins, F., Swaroop, A., Strong, L. C. & Saunders, G. F. (1991): Positional cloning and characterization of a paired box- and homeobox-containing gene from the aniridia region. *Cell* 67, 1059–1074

Treisman, J., Harris, E. & Desplan, C. (1991): The paired box encodes a second DNA-binding domain in the paired homeo domain protein. *Genes & Development* 5, 595–604 van der Mark, K., Kirsch, T., Aigner, T., Reichenberger, E., Nerlich, A., Wesloh, G. and Stoss, H. (1992): The fate of chondrocytes in osteoarthritic cartilage: Regeneration, differentiation, or hypertrophy? In "Articular Cartilage and Osteoarthritis" (K. Kuetner, R. Schleyerbach, J. G. Peyron, and V. C. Hascall, Eds.) pp. 221–234. Raven Press, New York Wallin, J., Mizutani, Y., Imai, K., Miyashita, N., Moriwaki, K., Taniguchi, M., Koseki, H. & Balling, R. (1993): A new Pax gene, Pax-9, maps to mouse chromosome 12. *Mammalian Genome* 4, 354–358

Walther, C., Guenet, J. L., Simon, D., Deutsch, U., Jostes, B., Goulding, M. D., Plachov, D., Balling, R. & Gruss, P. (1991): Pax: a multigene family of paired box-containing genes. *Genomics* 11: 424–434

Xu, W., Rould, M. A., Jun, S., Desplan, C. & Pabo, C. O. (1995): Crystal structure of a paired domain-DNA complex at 2,4A resolution reveals structural basis for Pax developmental mutations. *Cell* 80, 639–650

Zannini, M., Francis-Lang, H., Plachov, D. & Di Lauro, R. (1992): Pax-8, a paired domain-containing protein, binds to a sequence overlapping the recognition site of a homeodomain and activates transcription from two thyroid-specific promoters. *Mol. Cell. Biol.* 12, 4230–4241

What is claimed is:

1. A method for the detection of at least one tumorous and/or dysplastic stratified squamous epithelial cell in vitro comprising contacting a polyclonal or monoclonal antibody which specifically binds the Pax9 antigen within the amino acid sequence of amino acids 130–337 of SEQ ID NO:2 with a tissue sample containing an epithelial cell to be analyzed, and comparing at least one of the amount and localization of said Pax9 antigen in the nucleus and cytoplasm of said epithelial cell to the amount of said antigen in the nucleus and cytoplasm of a non-tumorous or non-dysplastic epithelial cell, wherein an increase in the amount or greater localization of said antigen in said cytoplasm of said cell or said tissue is an indication that said cell or said tissue is a tumor or dysplastic cell.

2. A method according to claim 1, characterized in that said amino acid sequence or polypeptide comprises amino acids 209–337 or 249–337 or 130–193 or 202–337 according to SEQ ID NO: 2.

3. A method according to claim 1 wherein said epithelial cell is from at least one tissue selected from the group consisting of oesophagus, skin, buccalmucosa, tongue, cornea, vagina, cervix, endometrium, and anus.

4. A monoclonal antibody which specifically binds the Pax9 antigen within the amino acid sequence of amino acids 130–337 of SEQ ID NO: 2.

5. A monoclonal antibody which specifically binds an epitope of a polypeptide wherein said epitope is contained in at least one sequence selected from the group consisting of amino acids 130–193, 202–337, 202–248, and 249–337 of SEQ ID NO: 2.

6. An analytical kit comprising a monoclonal antibody of claim 4.

7. A kit according to claim 6, comprising a monoclonal antibody which specifically binds to the amino acid sequence of amino acids 209–337 or 249–337 or 130–193 or 202–337 according to SEQ ID NO: 2.

8. A kit according to claim 6, further comprising reagents for analyzing binding of said antibody to a stratified squamous epithelial cell.

9. A kit according to claim 6, further comprising reagents for analyzing binding of said antibody to an epithelial cell of at least one tissue selected from the group consisting of the oesophagus, skin, buccalmucosa, tongue, cornea, vagina, cervix, endometrium, and anus.

10. A kit according to claim 6, further comprising reagents for analyzing binding of said antibody to a dysplastic stratified squamous epithelial cell.

11. A kit according to claim 6, further comprising reagents for analyzing binding of said antibody to a tumorous stratified squamous epithelial cell.

* * * * *